United States Patent
Kumagai et al.

(10) Patent No.: US 6,916,865 B2
(45) Date of Patent: Jul. 12, 2005

(54) ORGANIC CARBOXYLIC ACID SALT COMPOSITION, PROCESS FOR PREPARATION THEREOF AND ADDITIVES FOR EPOXY RESINS

(75) Inventors: Masashi Kumagai, Hitachi (JP); Takashi Ouchi, Kitaibaraki (JP); Katsuyuki Tsuchida, Kitaibaraki (JP)

(73) Assignee: Nikko Materials Co., Ltd., Tokyo (JP)

( * ) Notice: Subject to any disclaimer, the term of this patent is extended or adjusted under 35 U.S.C. 154(b) by 175 days.

(21) Appl. No.: 10/451,977

(22) PCT Filed: Aug. 27, 2002

(86) PCT No.: PCT/JP02/08621

§ 371 (c)(1),
(2), (4) Date: Jun. 25, 2003

(87) PCT Pub. No.: WO03/048171

PCT Pub. Date: Jun. 12, 2003

(65) Prior Publication Data

US 2004/0077751 A1 Apr. 22, 2004

(30) Foreign Application Priority Data

Dec. 6, 2001 (JP) ........................................ 2001-372646
May 21, 2002 (JP) ........................................ 2002-146195

(51) Int. Cl.$^7$ .................. C07D 213/69; C07D 233/72; C07D 235/12; C07F 7/10; C08K 5/11
(52) U.S. Cl. ........................ 523/455; 546/14; 548/110; 556/437; 556/440
(58) Field of Search ........................... 523/455; 546/14; 548/110; 556/437, 440

(56) References Cited

U.S. PATENT DOCUMENTS 6,710,181 B2 * 3/2004 Kumagai et al. ........... 548/110

FOREIGN PATENT DOCUMENTS

| | | | | |
|---|---|---|---|---|
| JP | 5-186479 | 7/1993 | | |
| JP | 6-279458 | 10/1994 | | |
| JP | 6-279463 | 10/1994 | | |
| JP | 9-12683 | 1/1997 | | |
| JP | 9-295988 | 11/1997 | | |
| JP | 9-295989 | 11/1997 | | |
| JP | 9-295990 | 11/1997 | | |
| JP | 9-295991 | 11/1997 | | |
| JP | 9-296135 | 11/1997 | | |
| JP | 09310043 A | * 12/1997 | ......... | C09D/143/04 |
| JP | 10-273492 | 10/1998 | | |
| JP | 2000-297094 | 10/2000 | | |
| JP | 2001-187836 | 7/2001 | | |
| JP | 2001-348393 | 12/2001 | | |
| WO | WO 01/77119 A1 | 10/2001 | | |

* cited by examiner

Primary Examiner—Robert Sellers
(74) Attorney, Agent, or Firm—Flynn, Thiel, Boutell & Tanis, P.C.

(57) ABSTRACT

The present invention provides an organic carboxylate composition that has long working life, cures epoxy resins, and improves adhesive properties, and also provides a method for producing the same. An organic carboxylate composition, obtained by heating and mixing a basic silane coupling agent and an amine compound with a softening point or melting point of 40° C. or greater together with an organic carboxylic acid; a method for producing the same; an additive for epoxy resin that contains this as the active ingredient thereof; and an epoxy resin composition containing the same. The basic silane coupling agent should preferably be a specific imidazole-group containing silane coupling agent, amino group-containing silane coupling agent, dialkylamino group-containing silane coupling agent, monomethylamino group-containing silane coupling agent, benzimidazole group-containing silane coupling agent, benzotriazole group-containing silane coupling agent, and pyridine ring-containing silane coupling agent.

6 Claims, No Drawings

ORGANIC CARBOXYLIC ACID SALT COMPOSITION, PROCESS FOR PREPARATION THEREOF AND ADDITIVES FOR EPOXY RESINS

TECHNICAL FIELD

The present invention relates to an organic carboxylate composition capable of exhibiting exceptional storage stability and enhanced adhesion as a coupling agent for powdered paints or as an additive for one-component epoxy resin compositions, and to a producing method and utilization thereof.

BACKGROUND ART

Imidazoles are curing agents that are receiving attention for providing exceptional curing properties to resin compositions, resulting in cured materials with high heat resistance. However, because of problems with storage stability, extending working life by controlling basicity is being investigated through formation of metal complexes and various types of acid salts. The inventors have filed patent applications (Japanese Patent Application Publication Nos. 9-12683 and 2000-297094) in which a mixture of the general formulas (1), (2), and (3) below or an imidazole group-containing silane coupling agent expressed by the general formula (4) would provide, as curing agents for epoxy resins, curable epoxy resin compositions having exceptional adhesion properties. However, these imidazole group-containing silane coupling agents are disadvantageous in having poor storage stability in the same manner as do conventional imidazoles.

Poor storage stability when mixed with epoxy resin is also a problem with silane coupling agents such as amino group-containing silane coupling agents (commercial products), dialkylamino group-containing silane coupling agents (Japanese Patent Application Publication Nos. 9-295988, 9-296135, and 9-295989), monomethylamino group-containing silane coupling agents (commercial products), benzimidazole group-containing silane coupling agents (Japanese Patent Application Publication No. 6-279458), benzotriazole group-containing silane coupling agents (Japanese Patent Application Publication No. 6-279463), or pyridine ring-containing silane coupling agents (Japanese Patent Application Publication Nos. 9-295990 and 9-295991).

DISCLOSURE OF THE INVENTION

An object of the present invention is to provide an organic carboxylate composition that is solid at room temperature, remains stable and has long working life when mixed with epoxy resin without compromising the improved adhesion characteristics of the above-mentioned silane coupling agents with respect to appropriate epoxy resins, melts at a prescribed temperature, and has silane coupling functionality capable of contributing to the curing reaction of the epoxy resins; to provide a method for producing the same; and to provide an additive for epoxy resin and an epoxy resin composition containing the same.

As a result of extensive investigation, the inventors discovered that a basic silane coupling agent organic carboxylate composition obtained by a specific method not only had exceptional curing properties and storage stability as an additive for epoxy resin, but also yielded a significant enhancement to adhesion properties. The present invention is based upon this discovery, and can be summarized as follows.

[1] An organic carboxylate composition, obtained by heating and mixing a basic silane coupling agent and an amine compound having a softening point or melting point of 40° C. or greater together with an organic carboxylic acid.

[2] A method for producing an organic carboxylate composition, comprising heating and mixing a basic silane coupling agent and an amine compound having a softening point or melting point of 40° C. or greater together with an organic carboxylic acid.

[3] The organic carboxylate composition according to [1], wherein the basic silane coupling agent is comprised of one compound or a mixture of two or more compounds selected from the group consisting of compounds expressed by the general formulas (1) through (4) below, or at least one selected from the group consisting of amino group-containing-silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents.

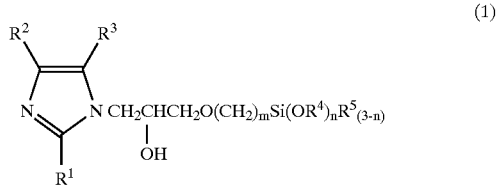

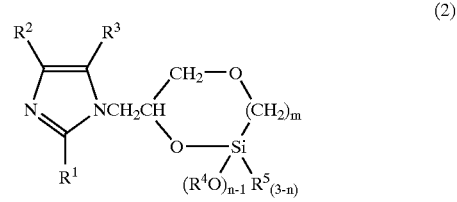

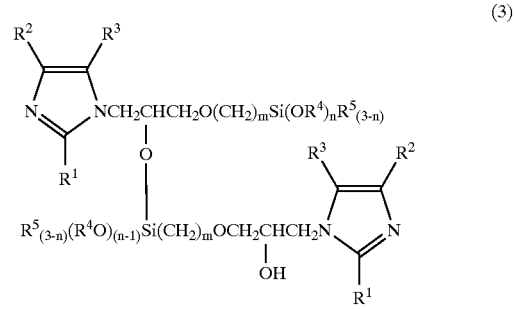

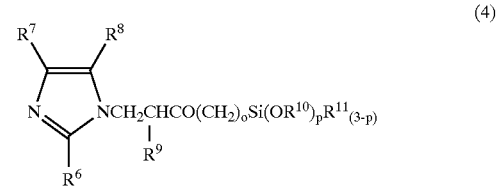

wherein in the formulas (1) through (3), $R^1$, $R^2$, and $R^3$ each represent hydrogen, a vinyl group, or an alkyl group having 1 to 20 carbon atoms and $R^2$ and $R^3$ may form an aromatic ring; $R^4$ and $R^5$ each represent an alkyl group having 1 to 5 carbon atoms; and m and n are integers of 1 to 10 and 1 to 3, respectively, and wherein in the formula (4), $R^6$, $R^7$, and $R^8$ each represent hydrogen, an alkyl group having 1 to 20 carbon atoms, a vinyl group, a phenyl group, or a benzyl group, and $R^7$ and $R^8$ may bond and form an aromatic ring; $R^9$ represents hydrogen or an alkyl group having 1 to 3 carbon atoms; $R^{10}$ and $R^{11}$ each represent an alkyl group having 1 to 5 carbon atoms; and o and p are integers of 1 to 10 and 1 to 3, respectively.

[4] A method for producing the organic carboxylate composition according to [2], wherein the basic silane coupling agent is comprised of one compound or a mixture of two or more compounds selected from the group consisting of compounds expressed by the general formulas (1) through (4) below, or at least one of amino group-containing silane coupling agents, dialkylamino group-containing silane coupling-agents, monomethylamino group-containing silane coupling agents, benzimidazole group-containing silane coupling agents, benzotriazole group-containing silane coupling agents, and pyridine ring-containing silane coupling agents.

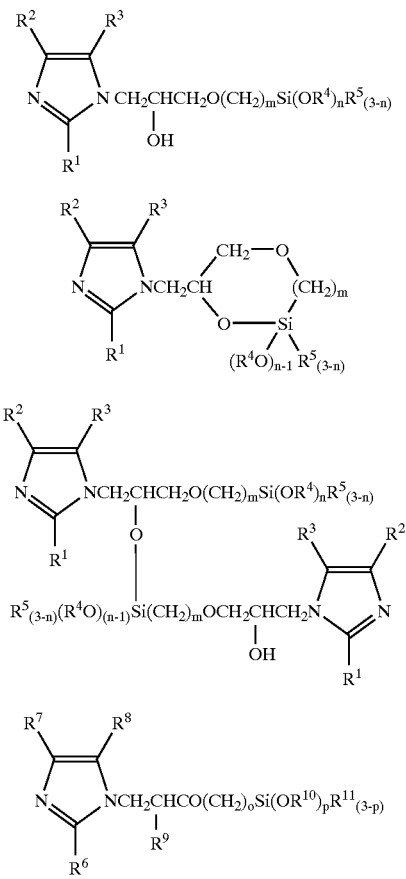

wherein the respective symbols in the formulas are the same as those shown in [3] above.

[5] An epoxy resin composition, containing the organic carboxylate composition according to [1] or [3].

[6] An additive for epoxy resin, containing the organic carboxylate composition according to [1] or [3].

The present invention will be described in further detail hereafter.

The basic silane coupling agent used in the production of the organic carboxylate composition of the present invention should preferably be a single compound or a mixture of two or more compounds selected from the group consisting of compounds expressed by the general formulas (1) through (4) above, or at least one selected from the group consisting of amino group-containing silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents.

The compounds expressed by the general formulas (1) through (3) above can be synthesized based on the method disclosed in Japanese Patent Application Publication No. 5-186479. The compound expressed by the general formula (4) above can be synthesized based on the method disclosed in Japanese Patent Application Publication No. 2000-297094. The compounds of the general formulas (1) through (3) above can be obtained as mixtures in the manner described in Japanese Patent Application Publication No. 5-186479, so there is no particular need to separate the mixtures, and the compounds should preferably be used as-is in the form of such mixtures.

Amino group-containing silane coupling agents include (3-aminopropyl)trimethoxysilane, (3-aminopropyl)triethoxysilane, (3-aminopropyl)dimethoxymethylsilane, (3-aminopropyl)diethoxymethylsilane, N-(2-aminoethyl)-3-aminopropyltrimethoxysilane, and the like. Monomethylamino group-containing silane coupling agents include N-methylaminopropyltrimethoxysilane, N-methylaminopropyltriethoxysilane, and the like. Dialkylamino group-containing silane coupling agents include those disclosed in Japanese Patent Application Publication Nos. 9-295988, 9-296135, and 9-295989. Among these, dimethylamino group-containing silane coupling agents are particularly preferred. Benzotriazole-containing silane coupling agents include those disclosed in Japanese Patent Application Publication No. 6-279463, benzimidazole group-containing silane coupling agents include those disclosed in Japanese Patent Application Publication No. 6-279458, and pyridine ring-containing silane coupling agents include those disclosed in Japanese Patent Application Publication Nos. 9-295990 and 9-295991.

The organic carboxylate composition of the present invention is obtained by a process in which the basic silane coupling agent and an amine compound with a softening point or melting point of 40° C. or greater are heated and mixed with an organic carboxylic acid at 50–200° C. If the softening point or melting point is less than 40° C., the resulting product is less amenable to hardening, and the hardened product is less amenable to pulverization.

Examples of amine compounds with a softening point or melting point of 40° C. or greater include imidazole compounds, aromatic amines, aliphatic amines, dicyandiamides, organic acid hydrazides, and modified polyamines. Specific Examples thereof are described in "Recent Development of Epoxy Resin Hardener" (compiled under the supervision of Hiroshi Kakiuchi, published by CMC, 1994).

Examples of imidazole compounds include 1H imidazole, 2-methylimidazole, 2-ethyl-4-methylimidazole, 2-phenylimidazole, 2-undecylimidazole, 2-heptadecylimidazole, 1-benzyl-2-methylimidazole, 2-phenyl-4-methylimidazole, 1-cyanoethyl-2-methylimidazole, 1-cyanoethyl-2-phenylimidazole, 1-cyanoethyl-2-ethyl-4-methylimidazole, and 1-cyanoethyl-undecylimidazole.

An aliphatic saturated carboxylic acid, aliphatic unsaturated carboxylic acid, aromatic carboxylic acid, or the like can be used as the organic carboxylic acid. Desirable organic carboxylic acids from among these include maleic acid, itaconic acid, azelaic acid, phthalic acid, acrylic acid, methacrylic acid, isobutyric acid, octylic acid, formic acid, glyoxylic acid, crotonic acid, acetic acid, propionic acid, benzoic acid, salicylic acid, cyclohexanecarboxylic acid, toluic acid, phenylacetic acid, p-t-butylbenzoic acid, trimellitic acid, trimellitic anhydride, cis-4-cyclohexene dicarboxylic acid, 2-octenyl succinic acid, 2-dodecenyl succinic acid, pyromellitic acid, and the like.

The reaction molar ratio of the basic silane coupling agent, the amine compound with a softening point or melting point of 40° C. or greater, and the organic carboxylic acid should preferably be such that at least one carboxyl group per mole of the organic carboxylic acid forms a salt with a base. The molar ratio of the combined number of moles of the basic silane coupling agent and the amine compound with a softening point or melting point of 40° C. or greater, and the organic carboxylic acid should be 1:0.1 to 1:5, and preferably 1:0.2 to 1:2. The molar ratio of the basic silane coupling agent and the amine compound with a softening point or melting point of 40° C. or greater should be established such that the organic carboxylate composition obtained by the heating and mixing procedure is in solid form at room temperature. The ratio is thus selected from a range of 5:1 to 1:5. The composition is less likely to be in solid form at room temperature if the molar ratio of the basic silane coupling agent exceeds this range, and the resulting silane coupling functions are inadequate if the molar ratio of the amine compound with a softening point or melting point of 40° C. or greater exceeds this range.

BEST MODE FOR CARRYING OUT THE INVENTION

Examples will be shown hereafter, and the present invention will be described in further detail. In the Examples that follow, "parts" designates "parts by weight."

Synthesis of Organic Carboxylate Composition

EXAMPLE 1

13.62 g (0.2 mol) of imidazole was melted at 95° C., and 47.27 g (0.2 mol) of (3-glycidoxypropyl)trimethoxysilane was added dropwise thereto over a period of 30 minutes while stirred in an argon atmosphere. Following addition, the product was further reacted for one hour at a temperature of 95° C., yielding an imidaz,ole group-containing silane coupling agent comprising a mixture of the compounds represented by the chemical formulas (1), (2), and (3) below. In the formulas (1), (2), and (3) below, $R^1$, $R^2$, and $R^3$ are H; $R^4$ is $CH_3$; n is 3; and m is 3. 2.16 g (0.04 mol) of the imidazole group-containing silane coupling agent thus obtained, 8.64 g (0.06 mol) of 2-phenylimidazole (melting point: 137–147° C.), and 21.0 g (0.1 mol) of trimellitic acid were heated and mixed at 160° C., the reaction was continues for one hour, and the product was cooled to room temperatures, yielding an imidazole trimellitate composition that was solid at normal temperature. The solid product thus obtained was ground with a mortar and classified by a sieve with hole openings of 90 microns to yield pulverized Sample No. 1.

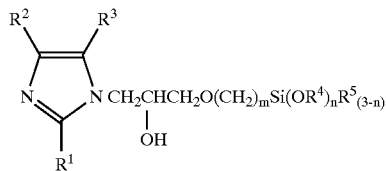

(1)

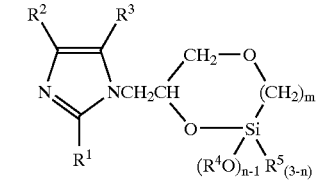

(2)

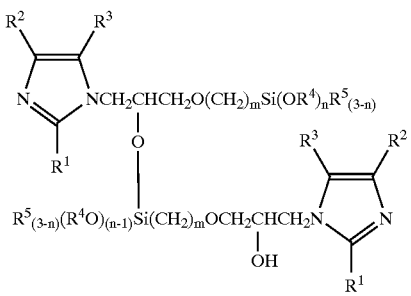

(3)

EXAMPLE 2

13.6 g (0.2 mol) of imidazole and 24.8 g (0.1 mol) of (3-methacryloxypropyl)trimethoxysilane were mixed and reacted at 100° C. for 11 hours. After cooling to room temperature, 100 ml of ethyl acetate was added, and excess imidazole was removed by washing the product three times in 100 ml of deionized water. Molecular sieves were added to the product, and the ethyl acetate solution was dried overnight. Subsequently, the ethyl acetate was distilled off in a rotary evaporator, and the imidazole group-containing silane coupling agent expressed by the formula (4) below was obtained. In the formula, $R^6$, $R^7$, and $R^8$ are H; $R^9$ is $CH_3$; $R^{10}$ is $CH_3$; o is 3; and p is 3. 12.64 g (0.04 mol) of the imidazole group-containing silane coupling agent thus obtained, 8.64 g (0.06 mol) of 2-phenylimidazole (melting point: 137–147° C.), and 21.0 g (0.1 mol) of trimellitic acid were heated and mixed at 160° C., the reaction was continued for one hour, and the product was cooled to room temperature, yielding an imidazole trimellitate composition that was solid at normal temperature. The solid product thus obtained was ground with a mortar and classified by a sieve with hole openings of 90 microns to yield pulverized Sample No. 2.

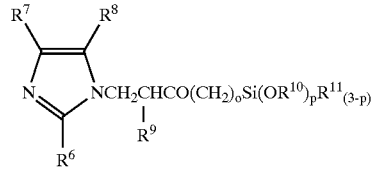

(4)

Evaluation of Adhesion Properties

EXAMPLE 3

Epoxy resin compositions containing Sample Nos. 1 and 2 obtained in Examples 1 and 2 were prepared, and the effect on adhesion properties was evaluated.

Epoxy Resin Composition:
Bisphenol A-type epoxy (Epikote 828, mfd. by Japan Epoxy Resins Co., Ltd.): 100 parts by weight
Dicyandiamide (AH-154, mfd. by Ajinomoto Co., Inc.): 5 parts by weight
2-Ethyl-4-methylimidazole (2E4MZ, mfd. by Shikoku Chemicals Corp.): 1 part by weight
Sample No. 1 or 2: 1 part by weight
Backing material: SUS304 (polished with No. 240 abrasive paper (in accordance with JIS K6848) immediately before use, and used after being cleaned with acetone) Dimensions 100×25×2 in thickness (mm)
Curing conditions: 100° C.×1 hour+150° C.×1 hour
Evaluation method: The epoxy resin composition was sandwiched between two SUS304 backing sheets, and shear adhesive strength was measured at a crosshead speed of 1 mm/min by means of a tensile tester following heating and curing (according to JIS K6850).

The evaluation results thus obtained are shown in Table 1.

COMPARATIVE EXAMPLES 1 AND 2

Epoxy resin compositions and bonded materials were prepared and evaluated as comparative examples in the same manner as in Example 3, except that the sample used in Example 3 was not added (Comparative Example 1) and one part of (3-glycidoxypropyl)trimethoxysilane was added (Comparative Example 2) instead of the above-mentioned sample. The obtained results are shown in Table 1.

TABLE 1

Effects of Adding Sample Nos. 1 and 2 on Shear Adhesive Strength

| | Additive | Shear adhesive strength(kN/cm$^2$) |
|---|---|---|
| Example 3 | Sample No. 1 | 1.38 |
| | Sample No. 2 | 1.36 |
| Comparative Example 1 | No additive | 1.02 |
| Comparative Example 2 | (3-glycidoxypropyl) trimethoxysilane | 1.11 |

Evaluation of Mechanical Characteristics of Cured Material

EXAMPLE 4

An epoxy resin cured material containing each of Sample Nos. 1 and 2, which were obtained in Examples 1 and 2, was prepared, and the effect on mechanical characteristics was evaluated.
Epoxy Resin Composition:
Bisphenol A-type epoxy (Epikote 828, mfd. by Japan Epoxy Resins Co., Ltd.): 100 parts by weight
Dicyandiamide (AH-154, mfd. by Ajinomoto Co., Inc.): 5 parts by weight
2-Ethyl-4-methylimidazole (2E4MZ, mfd. by Shikoku Chemicals Corp.): 1 part by weight
Sample No. 1 or 2: 1 part by weight
Granular silica filler (RD-8, mfd. by Tatsumori K. K.): 100 parts by weight
Dimensions of cured material: 80×10×4 in thickness (mm)
Curing conditions: 100° C.×1 hour+150° C.×1 hour
Evaluation method: Three-point flexural strength was measured at a crosshead speed of 2 mm/min at the loading point (in accordance with JIS K6911).

The evaluation results thus obtained are shown in Table 2.

COMPARATIVE EXAMPLES 3 AND 4

Epoxy resin cured materials were prepared and evaluated as comparative examples in the same manner as in Example 4, except that the sample used in Example 4 was not added (Comparative Example 3) and one part of (3-glycidoxypropyl)trimethoxysilane was added (Comparative Example 4) instead of the above-mentioned sample. The results are shown in Table 2.

TABLE 2

Effects of Adding Sample Nos. 1 and 2 on Flexural Strength of Cured Materials

| | Additive | Flexural strength (N/mm$^2$) |
|---|---|---|
| Example 4 | Sample No. 1 | 99.1 |
| | Sample No. 2 | 98.2 |
| Comparative Example 3 | No additive | 84.1 |
| Comparative Example 4 | (3-glycidoxypropyl) trimethoxysilane | 90.2 |

Evaluation of Storage Stability and Curing Acceleration

EXAMPLE 5

The epoxy resin composition shown below was prepared by adding each of Sample Nos. 1 and 2, and this composition was evaluated for storage stability on the basis of the viscosity change during storage at room temperature. Curing acceleration was also evaluated by measuring the gelation time on a hot plate that was set to 150° C. The results are shown in Table 3.
Epoxy Resin Composition:
Bisphenol A-type epoxy (Epikote 828, mfd. by Japan Epoxy Resins Co., Ltd.): 100 parts by weight
Dicyandiamide (AH-154, mfd. by Ajinomoto Co., Inc.): 5 parts by weight
Sample No. 1 or 2: 5 parts by weight

COMPARATIVE EXAMPLES 5 AND 6

Epoxy resin compositions were prepared and evaluated as comparative examples in the same manner as in Example 5, except that one part of 2-ethyl-4-methylimidazole (2E4MZ, mfd. by Shikoku Chemicals Corp.) was added (Comparative Example 5) instead of Sample No. 1 or 2 used in Example 5 and that the aforementioned samples were not added (Comparative Example 6). The evaluation results are shown in Table 3.

TABLE 3

Effects of Adding Sample Nos. 1 and 2 on Storage Stability of Epoxy Resin Compositions

| | Additive | Storage stability (viscosity change) | Curing acceleration (gelation time) |
|---|---|---|---|
| Example 5 | Sample No. 1 | No viscosity change during storage for 10 days | 10 min. and 23 sec. |
| | Sample No. 2 | | 7 min. and 54 sec. |
| Comparative Example 5 | 2-ethyl-4-methylimidazole | Hardened due to storage for 10 days | 2 min. and 11 sec. |
| Comparative Example 6 | No additive | No viscosity change during storage for 10 days | 20 min. and 28 sec. |

Evaluation of Heat Softening

EXAMPLE 6

The heat softening properties of Sample Nos. 1 and 2 were evaluated using a temperature-controlled hot plate. The results are shown in Table 4.

TABLE 4

Evaluation of Heat Softening Properties of Sample Nos. 1 and 2

| Sample No. | Heat softening temperature (° C.) |
| --- | --- |
| 1 | 110° C. |
| 2 | 90° C. |

Synthesis and Adhesion Evaluation of Organic Carboxylate

EXAMPLES 7–17

Organic carboxylate compositions were prepared and Sample Nos. 3–13 were obtained in the same manner as in Example 1 except for the use of the basic silane coupling agents, amine compounds with a softening point or melting point of 40° C. or greater, and organic carboxylic acids shown in Table 5 below.

TABLE 5

| Sample No. | |
| --- | --- |
| 3 | (3-aminopropyl)trimethoxysilane: 0.04 mol<br>2-Phenylimidazole (melting point: 137–147° C.): 0.06 mol<br>Trimellitic acid: 0.1 mol |
| 4 | N-methylaminopropyltrimethoxysilane: 0.04 mol<br>2-Phenylimidazole (melting point: 137–147° C.): 0.06 mol<br>Trimellitic acid: 0.1 mol |
| 5 | Benzotriazole group-containing silane coupling agent synthesized in Example 1 of Japanese Patent Application Publication No. 6-279463: 0.04 mol<br>2-Phenylimidazole (melting point: 137–147° C.): 0.06 mol<br>Trimellitic acid: 0.1 mol |
| 6 | Dimethylaminosilane synthesized in Reference Example 1 of Japanese Patent Application Publication No. 9-296135: 0.04 mol<br>2-Phenylimidazole (melting point: 137–147° C.): 0.06 mol<br>Trimellitic acid: 0.1 mol |
| 7 | Benzimidazole group-containing silane coupling agent synthesized in Example 1 of Japanese Patent Application Publication No. 6-279458: 0.04 mol<br>2-Phenylimidazole (melting point: 137–147° C.): 0.06 mol<br>Trimellitic acid: 0.1 mol |
| 8 | Pyridine ring-containing silane coupling agent synthesized in Example 1 of Japanese Patent Application Publication No. 9-295991: 0.04 mol<br>2-Phenylimidazole (melting point: 137–147° C.): 0.06 mol<br>Trimellitic acid: 0.1 mol |
| 9 | Imidazole group-containing silane coupling agent obtained in the same manner as in Example 1: 0.04 mol<br>Diaminodiphenyl methane (melting point 89° C.): 0.06 mol<br>Trimellitic acid: 0.1 mol |
| 10 | Imidazole group-containing silane coupling agent obtained in the same manner as in Example 1: 0.04 mol<br>Diaminodicyclohexyl methane (melting point 40° C.): 0.06 mol<br>Trimellitic acid: 0.1 mol |
| 11 | Imidazole group-containing silane coupling agent obtained in the same manner as in Example 1: 0.04 mol<br>Dicyandiamide (melting point 207–210° C.): 0.06 mol<br>Trimellitic acid: 0.1 mol |
| 12 | Imidazole group-containing silane coupling agent obtained in the same manner as in Example 1: 0.04 mol<br>Adipic hydrazide (melting point 178° C.): 0.06 mol<br>Trimellitic acid: 0.1 mol |
| 13 | Imidazole group-containing silane coupling agent obtained in the same manner as in Example 1: 0.04 mol<br>Modified polyamine (polyaminoimide obtained from tetracarboxylic acid, ATI-2) (melting point 270° C.): 10 g<br>Trimellitic acid: 0.1 mol |

Using the samples thus obtained, epoxy resin compositions were produced and shear adhesive strength was evaluated in the same manner as in Example 3. The results are shown in Table 6 below.

TABLE 6

| | Additive | Shear adhesive strength (kN/cm$^2$) |
| --- | --- | --- |
| Example 7 | Sample 3 | 1.24 |
| Example 8 | Sample 4 | 1.26 |
| Example 9 | Sample 5 | 1.20 |
| Example 10 | Sample 6 | 1.42 |
| Example 11 | Sample 7 | 1.40 |
| Example 12 | Sample 8 | 1.32 |
| Example 13 | Sample 9 | 1.37 |
| Example 14 | Sample 10 | 1.30 |
| Example 15 | Sample 11 | 1.44 |
| Example 16 | Sample 12 | 1.33 |
| Example 17 | Sample 13 | 1.28 |

INDUSTRIAL APPLICABILITY

The organic carboxylate composition of the present invention is solid at room temperature and can function as a silane coupling agent. Applications thereof include not only functioning as an exceptional adhesion enhancer when added to a one-component resin composition, but also being able to impart long working life due to being solid at room temperature and having an organic carboxylate structure. The composition can also be pulverized and used in powdered coating materials because the heat softening temperature thereof is relatively high. In addition, the adhesiveness, mechanical properties, and storage stability of the composition allow this composition to be applied to the required epoxy resin compositions in a wide range of possible applications, including adhesives, paints, laminates, molding, printed wiring boards, copper-clad laminates, resin-coated copper foil, semiconductor chip coating materials, semiconductor chip mounting materials, photoresists, solder resists, dry film resists, and the like.

What is claimed is:

1. An organic carboxylate composition, obtained by heating and mixing a basic silane coupling agent and an amine compound having a softening point or melting point of 40° C. or greater together with an organic carboxylic acid.

2. A method for producing an organic carboxylate composition, comprising heating and mixing a basic silane coupling agent and an amine compound having a softening point or melting point of 40° C. or greater together with an organic carboxylic acid.

3. The organic carboxylate composition according to claim 1, wherein the basic silane coupling agent is comprised of one compound or a mixture of two or more compounds selected from the group consisting of compounds expressed by the general formulas (1) through (4) below, or at least one selected from the group consisting of amino group-containing silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents,

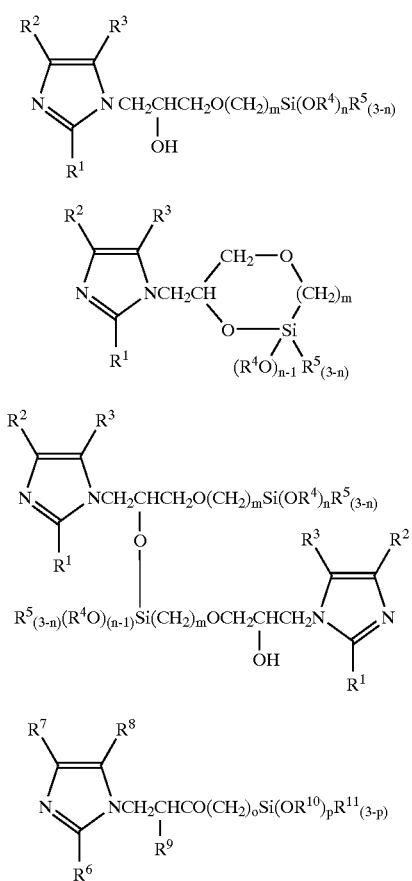

(1)

(2)

(3)

(4)

wherein in the formulas (1) through (3), $R^1$, $R^2$, and $R^3$ each represent hydrogen, a vinyl group, or an alkyl group having 2 to 20 carbon atoms and $R^2$ and $R^3$ may form an aromatic ring; $R^4$ and $R^5$ each represent an alkyl group having 1 to 5 carbon atoms; and m and n are integers off 1 to 10 and 1 to 3, respectively, and wherein in the formula (4), $R^6$, $R^7$, and $R^8$ each represent hydrogen, an alkyl group having 1 to 20 carbon atoms, a vinyl group, a phenyl group, or a benzyl group, and $R^7$ and $R^8$ may bond and form an aromatic ring; $R^9$ represents hydrogen or an alkyl group having 1 to 3 carbon atoms; $R^{10}$ and $R^{11}$ each represent an alkyl group having 1 to 5 carbon atoms; and a and p are integers of 1 to 10 and 1 to 3, respectively.

4. A method for producing the organic carboxylate composition according to claim 2, wherein the basic silane coupling agent is comprised of one compound or a mixture of two or more compounds selected from the group consisting of compounds expressed by the general formulas (1) through (4) below, or at least one selected from the group consisting of amino group-containing silane coupling agents, dialkylamino group-containing silane coupling agents, monomethylamino group-containing silane coupling agents, benzimidazole group-containing silane coupling agents, benzotriazole group-containing silane coupling agents, and pyridine ring-containing silane coupling agents,

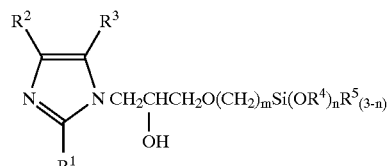

(1)

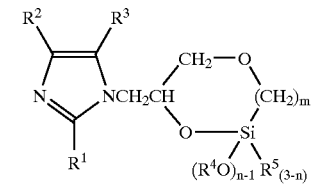

(2)

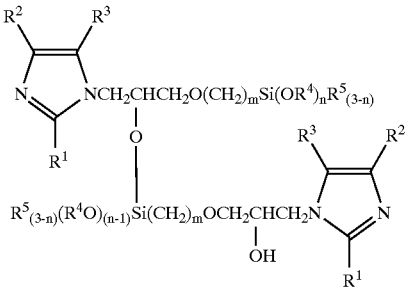

(3)

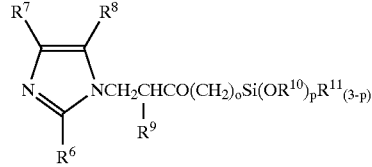

(4)

wherein in the formulas (1) through (3), $R^1$, $R^2$, and $R^3$ each represent hydrogen, a vinyl group, or an alkyl group having 1 to 20 carbon atoms and $R^2$ and $R^3$ may form an aromatic ring; $R^4$ and $R^5$ each represent an alkyl group having 1 to 5 carbon atoms; and m and n are integers of 1 to 10 and 1 to 3, respectively, and wherein in the formula (4), $R^6$, $R^7$ and $R^8$ each represent hydrogen, an alkyl group having 1 to 20 carbon atoms, a vinyl group, a phenyl group, or a benzyl group, and $R^7$ and $R^8$ may bond and form an aromatic ring; $R^9$ represents hydrogen or an alkyl group having 1 to 3 carbon atoms; $R^{10}$ and $R^{11}$ each represent an alkyl group having 1 to 5 carbon atoms; and o and p are integers of 1 to 10 and 1 to 3, respectively.

5. An epoxy resin composition, containing the organic carboxylate composition according to claim 1.

6. An additive for epoxy resin, containing the organic carboxylate composition according to claim 1.

* * * * *